(12) United States Patent  
Scardino et al.

(10) Patent No.: US 6,308,509 B1  
(45) Date of Patent: Oct. 30, 2001

(54) FIBROUS STRUCTURES CONTAINING NANOFIBRILS AND OTHER TEXTILE FIBERS

(75) Inventors: Frank L. Scardino, Penllyn; Richard J. Balonis, Croydon, both of PA (US)

(73) Assignee: Quantum Group, Inc, Colfax, NC (US)

(*) Notice: Subject to any disclaimer, the term of this patent is extended or adjusted under 35 U.S.C. 154(b) by 0 days.

(21) Appl. No.: 09/621,856

(22) Filed: Jul. 24, 2000

Related U.S. Application Data

(62) Division of application No. 09/169,116, filed on Oct. 8, 1998, now Pat. No. 6,106,913.
(60) Provisional application No. 60/061,611, filed on Oct. 10, 1997.

(51) Int. Cl.$^7$ ........................................... D01H 4/28
(52) U.S. Cl. ................................................. 57/402
(58) Field of Search .......................... 57/402, 362, 400, 57/5, 401

(56) References Cited

U.S. PATENT DOCUMENTS

| | | | |
|---|---|---|---|
| 3,577,720 | * | 5/1971 | Zax et al. ............................... 57/403 |
| 3,670,486 | * | 6/1972 | Murray, Jr. ............................. 57/402 |
| 3,848,403 | * | 11/1974 | Bobkowicz et al. ...................... 57/5 |
| 3,901,012 | * | 8/1975 | Safar ..................................... 57/402 |
| 4,028,871 | * | 6/1977 | Aschenbrenner ....................... 57/402 |
| 4,362,008 | * | 12/1982 | Parker et al. ............................. 57/5 |
| 4,468,922 | * | 9/1984 | McCrady et al. ....................... 57/402 |
| 4,965,110 | * | 10/1990 | Berry ................................. 428/36.4 |
| 5,024,789 | * | 6/1991 | Berry ........................................ 264/6 |
| 6,106,913 | * | 8/2000 | Scardino et al. ..................... 428/36.3 |

FOREIGN PATENT DOCUMENTS

1349925 * 4/1974 (GB) .................................... 57/402

* cited by examiner

Primary Examiner—Danny Worrell  
(74) Attorney, Agent, or Firm—John S. Munday

(57) ABSTRACT

Nanofibers are produced having a diameter ranging from about 4 Å to 1 nm, and a nano denier of about $10^{-9}$. The use of the electro-spinning process permits production of the desired nanofibrils. These fibrils in combination with a carrier or strengthening fibers/filaments can be converted directly into nonwoven fibrous assemblies or converted into linear assemblies(yarns) before weaving, braiding or knitting into 2-dimensional and 3-dimensional fabrics. The electrospun fiber can be fed in an air vortex spinning apparatus developed to form a linear fibrous assembly. The process makes use of an air stream in a properly confined cavity. The vortex of air provides a gentle means to convert a mixture of the fibril fed directly or indirectly from the ESP unit and a fiber mass or filament into an integral assembly with proper level of orientation. Incorporation of thus produced woven products into tissue engineering is part of the present invention.

6 Claims, 1 Drawing Sheet

FIBROUS STRUCTURES CONTAINING NANOFIBRILS AND OTHER TEXTILE FIBERS

This application is a division of Ser. No. 09/169,116 filed Oct. 8, 1998, U.S. Pat. No. 6,106,913 which claims benefit of Provisional No. 60/061,611 filed Oct. 10, 1997.

FIELD OF THE INVENTION

The present invention is directed towards an improved fibrous structure. More particularly, the present invention relates to linear two-dimensional and three-dimensional textile structures.

BACKGROUND OF THE INVENTION

Linear, 2-dimensional and 3-dimensional textile structures have found new uses beyond traditional apparel in recent years because of their unique combination of light weight, flexibility, permeability, and strength and toughness. Many of these applications including but not limited to medical, chemical separation, chemical protection require a broad range of fiber architecture, packing density, surface texture, porosity, total reactive surface areas and fiber tortuosity.

Some early work on fiber structures are discussed in an article by Frank K. Ko entitled Three Dimensional Fabrics for Composites, in *Textile Structural Composites*, Chou, T. W., and Ko, F. K., eds., Elsevier, 1989. Another discussion of the prior art is by Frank K. Ko entitled Preform Fiber Architecture for Ceramic Matrix Composites, *Bull Am. Cer. Soc.* February, 1989.

A key element dictating the range of these physical characteristics is the fineness (diameter, linear density-denier) of the constituent fibers and the way these fibers are organized and oriented. For many years, the range of fiber fineness expressed in terms of fiber diameter are well above 2 $\mu$m.

It would be of great advantage in the art if fibers of smaller diameter could be prepared for these applications. Another advantage would be if those smaller fibers could be made stronger.

Accordingly, it is an object of the present invention to provide a method of making fibers of much smaller diameter, in the range of what are known as nanofibrils.

Another object of this invention is to provide nanofibrils with adequate strength to permit their use in textile processing processes.

Other objects will appear hereinafter.

SUMMARY OF THE INVENTION

It has now been discovered that the above and other objects of the present invention may be accomplished in the following manner. Specifically, it has been discovered that it is now possible to produce fibrils—fibers in the nanometer diameter level.

One current limitation of these fibrils is their lack of sufficient strength to withstand the rigors of textile processing. The fineness of these fibrils also make them prone to stick to surfaces during process. The lack of strength can be remedied by combining the fibrils with stronger fibers or filaments. The problems caused by surface contacts can be minimized by a pneumatic(air) or fluid based processing of the fibrils. These fibrils in combination with the carrier or strengthening fibers/filaments can be converted directly into nonwoven fibrous assemblies or converted into linear assemblies(yarns) before weaving, braiding or knitting into 2-dimensional and 3-dimensional fabrics. The use of the electro-spinning process permits production of the desired nanofibrils.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Textile fibers have a fiber diameter ranging from 1 $\mu$m to 10 $\mu$m, and a denier ranging from $10^{-3}$ to 10. The lower diameters and deniers are mostly electrospun fibers, with nothing below 100 nm (nanometer) in fiber diameter or $10^{-5}$ denier having been developed. Nanofibers, in accordance with the present invention, have a diameter ranging from about 4 Å to 1 nm, and a nano denier of about $10^{-9}$.

The present invention permits the production of 2-dimensional and 3-dimensional products including nanofibers by the use of the electrospinning process. This spinning process makes it possible to produce fibrils—fibers in the nanometer diameter range. It has been discovered that the inherent lack of strength of these very fine fibrils can be remedied by combining the fibrils with stronger fibers or filaments. It has also been found that problems caused by surface contacts can be minimized by a pneumatic or fluidic processing of the fibrils. The fibrils of this invention can, in combination with the carrier or strengthening fibers/filaments be converted directly into nonwoven fibrous assemblies or converted into linear assemblies or yarns before weaving, braiding or knitting into 2-dimensional and 3-dimensional fabrics.

Figure 1:
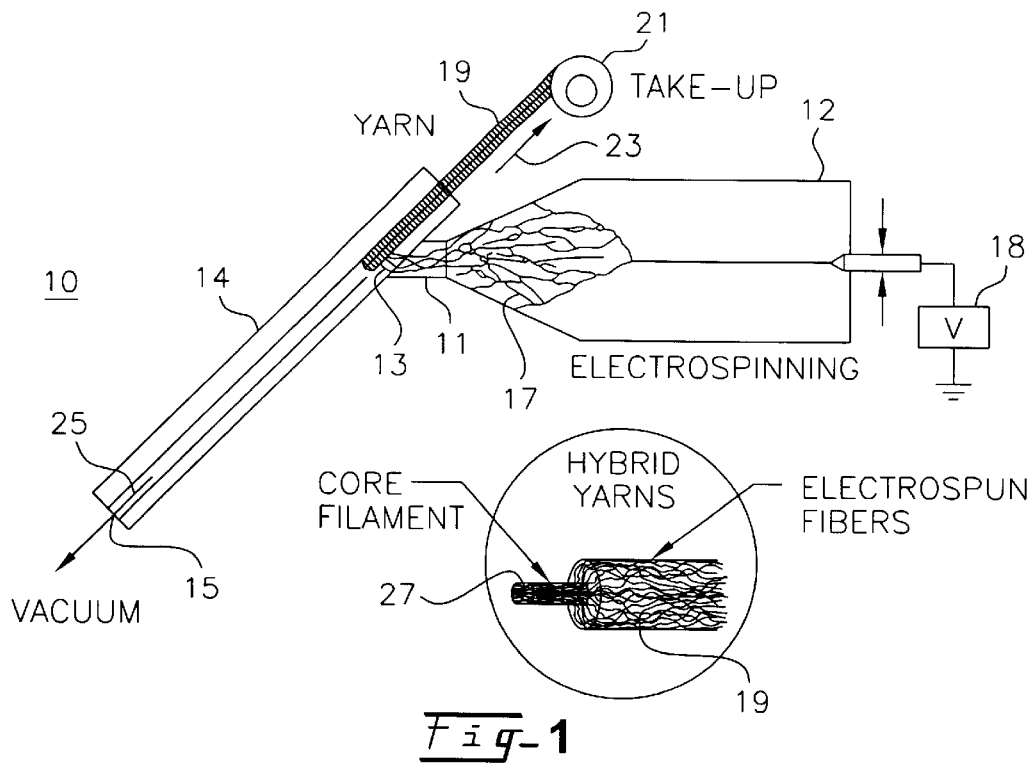
FIG. 1 is a schematic diagram of a hybrid yarn spinning system in accordance with the present invention.

The Air Vortex Spinning (AVS) Process used to form nanofibers is shown in FIG. 1. The electrospun fiber can be fed in an air vortex spinning apparatus developed to form a linear fibrous assembly, as illustrated in FIG. 1. The process makes use of an air stream in a properly confined cavity. The vortex of air provides a gentle means to convert a mixture of the fibril fed directly or indirectly from the ESP unit and a fiber mass or filament into an integral assembly with proper level of orientation.

Turning now to FIG. 1, the operation of the AVS, 10 generally, is described in more detail In its simplified form the AVS uses the principle of an air vortex created helical current, which current is responsible for the amount of twist and entanglement which is forwarded to the yarn. The air vortex helical current is created by a tangential influx of air pressure via inlet 11 from an electrostatic chamber 12 by a tangential influx of air pressure into the top of the spinning zone 13, comprising a spinning tube 14, and also including an air suction outlet 15 at the bottom of the spinning tube 14. Thus a helical as well as a vortex type velocity current is created inside zone 13. Twist and entanglement is imparted to the yarn by this mechanism. Control of these initial factors control the final structure of the yarn assembly.

At the point of introduction of fibers 17 via inlet 11, those fibers 17 have been electrostatically charged by electrostatic current source 18, and are then whirled in a looped configuration in the helical-vortex air current, at the open end or tail section of the yarn 19. By means of the aforementioned air current, fibers are simultaneously transferred, attached, twisted, and drawn off in the form of yarn 19. on to a take-up roll 21. Input tube 11 introduces fibers 17 at an acute angle tangential to the axis of spinning zone 13, and may be supplied from various sources such as containers of fibers or fiber rolls (not shown) or other fiber sources. The fibers 17 are, of course, the nanofibers described above having a diameter ranging from about 4 Å to 1 nm, and a nano denier of about $10^{-9}$.

The above described vortex air suction not only whirls the tail end of the yarn 19 to effect a twist it also draws new fibers 17 to be successively twisted into such a construction. As the yarn 19 is being drawn off in an axial direction 23 opposite to that of the helically created current 25, the helically created current imparts further twist to the construction, in a manner which may be described as whipping the yarn 19 around in a wave-like configuration. Since only one end of the yarn 19 is being held, further twist can be imparted to the system without being lost.

To demonstrate the efficacy of the present invention, a device was created including a Y-shaped glass tube 14 to form spinning zone 13. Air vortex suction was created by a variably controlled air pressure flowing across orifice 15 to cause a vacuum or suction within spinning zone 13. Fibers 17 were electrostatically charged by source 18 and then were directed from the fiber source to the spinning zone 13 by means of the air pressure suction. Various tests were made to study the effects of air pressure, air velocity, yarn linear density, take-off speed form the fiber source, and apparent twist of the yarn 19.

In FIG. 1, a core filament 27 is used as a core for the thus produced yarn 19, to form what may be designated as a hybrid yarn containing the core filament 27 and fibers 17 affixed thereto as described above. Examples of some textile fabric architecture that are suitable for the present invention are: biaxial woven, high modulus woven, multilayer woven, triaxial woven, tubular braid, tubular braid laid in warp, flat braid, flat braid laid in warp, weft knit, weft knit laid in weft, weft knit laid in warp, weft knit laid in weft laid in warp, square braid, square braid laid in warp, 3-dimensional braid, 3-dimensional braid laid in warp, warp knit, warp knit laid in warp, weft inserted warp knit, weft inserted warp knit laid in warp, fiber mat, stitchbonded laid in warp, biaxial bonded, and xyz laid in system.

Figure 2:
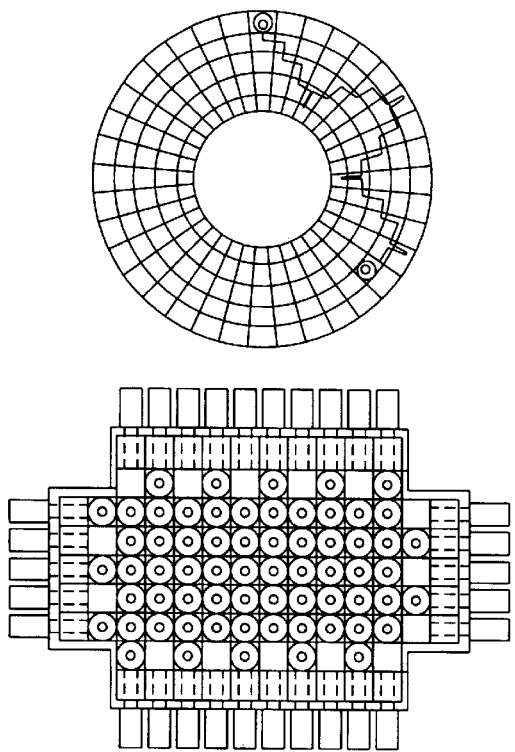
FIG. 2 is a schematic illustration of nanofiber fabrication in a circular or rectangular loom.
Figure 3:
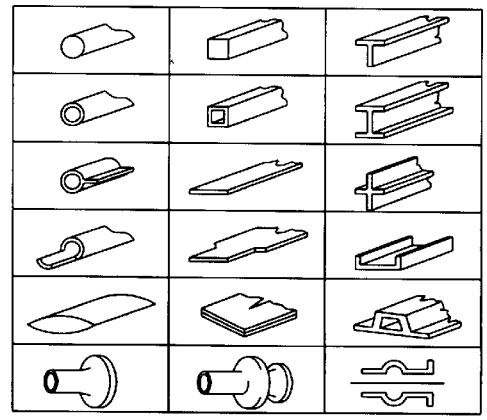
FIG. 3 is a schematic illustration of various 3-dimensional shapes that have been fabricated in accordance with the invention.
Figure 3:
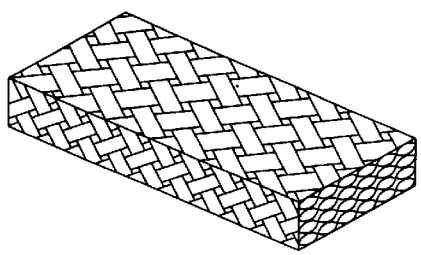

An Example of 3D braiding technology is an extension of the traditional 2-dimensional braiding technology in which the fabric is constructed by the intertwining or orthogonal interlacing of yarns to form an integral structure through position displacement Fabricated in a circular or rectangular loom, shown in FIG. 2, a wide range of 3-dimensional shapes shown in FIG. 3 have been fabricated as part of the work herein. The resulting linear fiber assembly or yarn is a hybrid of nano- and micro fibers with a strong core filament, thus combining texture surfaces and strength in one assembly. By properly controlling the processing conditions a wide variety of available surfaces, micro porosity and strength can be tailored.

Depending on the tissue to be engineered, the linear fibrous assemblies can be fabricated into a wide variety of planar and 3-dimensional fibrous assemblies by the textile manufacturing method. Depending on the manufacturing process, the resulting fiber architecture can be tailored using the porosity and tortuosity of these 3-dimensional fibrous structures. They can be tailored by selecting different yarn sizes and yarn orientation. This technology can be illustrated with the 3-dimensional braided structures shown herein. 3-dimensional braiding is attractive because of its versatility in designing microstructure and its capability of assuming net structural shapes.

The resulting linear fiber assembly or yarn will be a hybrid of nano- and micro fibers with a strong core filament, thus combining texture surfaces and strength in one assembly. By properly controlling the processing conditions a wide variety of available surfaces, micro porosity and strength can be tailored for tailored properties and performance. Combination of nanofibrils with stronger fibers and filaments Methods for converting nanofibrils into linear, planar, and 3-D fibrous assemblies One important embodiment of the present invention is the use of nanofibers in medical implant surgery. It is well known that biological tissues consist of well organized hierarchical fibrous structures realign from nano to mm scale. The successful regeneration of biological tissue and organs calls for the development of fibrous structures with fiber architectures conducive to cell deposition and cell proliferation. Of particular interest in tissue engineering is the creation of reproducible and biocompatible 3-dimensional scaffolds for cell ingrowth resulting in biomatrix composites for various tissue repair and replacement procedures. The present invention is admirable suited for that technique.

Many of the aforementioned textile architectures are suitable for tissue engineering applications with nanofibrils. This requires a thorough understanding of the structural geometry, including fiber tortuosity and fabric porosity as characterized by a fiber volume fraction-orientation analysis.

To demonstrate the efficacy of this procedure, PLAGA bioabsorbable polymer was placed in spherical, nanofibrils and aligned and 3-dimensionally braided with 20 $\mu$m filaments seeded with osteoblasts over a two week period, resulting in complete success of the procedure.

While particular embodiments of the present invention have been illustrated and described, it is not intended to limit the invention, except as defined by claims appended hereto.

What is claimed is:

1. Apparatus for forming a textile structure, comprising:
   a source of fibers having a diameter ranging from about 4 angstroms to 1 nm, and a nano denier of about 10–9;
   means for electrostatically charging said fibers and transferring said charged fibers;
   a vortex tube for forming an air vortex created helical current formed by air suction at one end of said tube;
   inlet means drawing said charged fibers into said tube to cause said fibers in said air vortex created helical current into contact with one another to form a yarn;
   outlet means drawing said yarn from the other end of said air vortex helical current tube; and
   fabrication means for receiving said yarn and forming said yarn into a textile structure.

2. The apparatus of claim 1, wherein said textile structure is two dimensional.

3. The apparatus of claim 1, wherein said textile structure is three dimensional.

4. The apparatus of claim 1, wherein said textile structure is formed into a structure having a 30 shape.

5. The apparatus of claim 4, wherein said structure is fabricated using a circular loom.

6. The apparatus of claim 4, wherein said structure is fabricated using a rectangular loom.

* * * * *